(12) United States Patent
Prakash et al.

(10) Patent No.: US 10,736,694 B2
(45) Date of Patent: *Aug. 11, 2020

(54) ELECTROSURGICAL DEVICES WITH DIRECTIONAL RADIATION PATTERN

(71) Applicant: COVIDIEN LP, Mansfield, MA (US)

(72) Inventors: Mani N. Prakash, Boulder, CO (US); Francesca Rossetto, Longmont, CO (US); Joseph D. Brannan, Lyons, CO (US)

(73) Assignee: COVIDIEN LP, Mansfield, MA (US)

( * ) Notice: Subject to any disclaimer, the term of this patent is extended or adjusted under 35 U.S.C. 154(b) by 848 days.

This patent is subject to a terminal disclaimer.

(21) Appl. No.: 15/382,954

(22) Filed: Dec. 19, 2016

(65) Prior Publication Data

US 2017/0100193 A1 Apr. 13, 2017

Related U.S. Application Data

(60) Continuation of application No. 14/242,048, filed on Apr. 1, 2014, now Pat. No. 9,526,575, which is a
(Continued)

(51) Int. Cl.
*A61B 18/18* (2006.01)
*A61B 18/14* (2006.01)
*A61B 18/00* (2006.01)

(52) U.S. Cl.
CPC ...... *A61B 18/1815* (2013.01); *A61B 18/1492* (2013.01); *A61B 18/18* (2013.01);
(Continued)

(58) Field of Classification Search
CPC ...... A61B 2018/1869; A61B 2018/183; A61B 2018/1853; A61B 2018/1861; A61B 18/1815
See application file for complete search history.

(56) References Cited

U.S. PATENT DOCUMENTS 3,870,977 A   3/1975 Peoples et al.
4,204,549 A   5/1980 Paglione
(Continued)

FOREIGN PATENT DOCUMENTS

DE   390937 C    3/1924
DE   1099658 B   2/1961
(Continued)

OTHER PUBLICATIONS

European Search Report EP 04027314 dated Mar. 31, 2005.
(Continued)

*Primary Examiner* — Jaymi E Della (57) ABSTRACT

A device for directing energy to a target volume of tissue includes an antenna assembly and an elongated body member. The elongated body member includes a proximal end portion and a distal end portion, wherein the proximal and distal end portions define a longitudinal axis. The elongated body member has a chamber defined therein that extends along the longitudinal axis, and a body wall surrounding the chamber. An antenna assembly is disposed in the chamber. The elongated body member also includes an opening in the body wall to allow energy radiated from the antenna assembly to transfer into the target volume of tissue.

10 Claims, 6 Drawing Sheets

Related U.S. Application Data division of application No. 13/567,624, filed on Aug. 6, 2012, now Pat. No. 8,690,869, which is a continuation of application No. 12/476,960, filed on Jun. 2, 2009, now Pat. No. 8,235,981.

(52) U.S. Cl.
CPC .............. A61B 2018/00023 (2013.01); A61B 2018/00077 (2013.01); A61B 2018/00083 (2013.01); A61B 2018/00351 (2013.01); A61B 2018/00577 (2013.01); A61B 2018/00589 (2013.01); A61B 2018/00601 (2013.01); A61B 2018/1861 (2013.01)

(56) References Cited

U.S. PATENT DOCUMENTS

| | | |
|---|---|---|
| 4,311,154 A | 1/1982 | Sterzer et al. |
| 4,743,725 A | 5/1988 | Risman |
| 4,754,752 A | 7/1988 | Ginsburg et al. |
| 4,825,880 A | 5/1989 | Stauffer et al. |
| 4,934,365 A | 6/1990 | Morgenthaler |
| 5,041,089 A | 8/1991 | Mueller et al. |
| 5,057,106 A | 10/1991 | Kasevich et al. |
| 5,097,845 A | 3/1992 | Fetter et al. |
| 5,249,585 A | 10/1993 | Turner et al. |
| 5,369,251 A | 11/1994 | King et al. |
| 5,500,012 A | 3/1996 | Brucker et al. |
| 5,588,432 A | 12/1996 | Crowley |
| 5,658,278 A | 8/1997 | Imran et al. |
| 5,776,176 A | 7/1998 | Rudie |
| 6,097,985 A | 8/2000 | Kasevich et al. |
| 6,181,970 B1 | 1/2001 | Kasevich |
| 6,230,060 B1 | 5/2001 | Mawhinney |
| 6,233,490 B1 | 5/2001 | Kasevich |
| 6,289,249 B1 | 9/2001 | Arndt et al. |
| 6,383,182 B1 | 5/2002 | Berube et al. |
| 6,471,696 B1 | 10/2002 | Berube et al. |
| 6,592,579 B2 | 7/2003 | Arndt et al. |
| 6,622,731 B2 | 9/2003 | Daniel et al. |
| 7,538,038 B2 | 5/2009 | Matsushita et al. |
| 7,642,451 B2 | 1/2010 | Bonn |
| 8,035,570 B2 | 10/2011 | Prakash et al. |
| 8,059,059 B2 | 11/2011 | Bonn |
| 8,118,808 B2 | 2/2012 | Smith et al. |
| 8,182,480 B2 | 5/2012 | Huseman |
| 8,192,427 B2 | 6/2012 | Buysse |
| 8,197,473 B2 | 6/2012 | Rossetto et al. |
| 8,202,270 B2 | 6/2012 | Rossetto et al. |
| 8,211,098 B2 | 7/2012 | Paulus |
| 8,211,099 B2 | 7/2012 | Buysse et al. |
| 8,221,418 B2 | 7/2012 | Prakash et al. |
| 8,235,981 B2 | 8/2012 | Prakash et al. |
| 8,246,614 B2 | 8/2012 | DeCarlo |
| 8,251,987 B2 | 8/2012 | Willyard |
| 8,262,703 B2 | 9/2012 | Prakash et al. |
| 8,292,880 B2 | 10/2012 | Prakash et al. |
| 8,292,881 B2 | 10/2012 | Brannan et al. |
| 8,343,149 B2 | 1/2013 | Rossetto et al. |
| 8,690,869 B2 | 4/2014 | Prakash et al. |
| 9,526,575 B2 | 12/2016 | Prakash et al. |
| 2002/0087151 A1 | 7/2002 | Mody et al. |
| 2002/0128642 A1 | 9/2002 | Berube et al. |
| 2003/0032951 A1 | 2/2003 | Rittman et al. |
| 2003/0036754 A1 | 2/2003 | Erb et al. |
| 2004/0049254 A1 | 3/2004 | Longo |
| 2006/0138122 A1* | 6/2006 | Gauthier ............ A61B 18/1492 219/543 |
| 2006/0289528 A1 | 12/2006 | Chiu et al. |
| 2007/0185554 A1 | 8/2007 | Appling et al. |
| 2007/0287998 A1 | 12/2007 | Sharareh et al. |
| 2008/0147056 A1 | 6/2008 | van der Weide et al. |
| 2008/0275436 A1 | 11/2008 | Cronin et al. |
| 2009/0187180 A1 | 7/2009 | Brannan |
| 2009/0192510 A1 | 7/2009 | Bahney |
| 2009/0198227 A1 | 8/2009 | Prakash |
| 2009/0222022 A1 | 9/2009 | Laporte Rosello et al. |
| 2009/0248005 A1 | 10/2009 | Rusin et al. |
| 2009/0248006 A1* | 10/2009 | Paulus ................ A61B 18/18 606/33 |
| 2009/0295674 A1 | 12/2009 | Bonn |
| 2009/0306652 A1 | 12/2009 | Buysse et al. |
| 2010/0030206 A1 | 2/2010 | Brannan et al. |
| 2010/0030208 A1 | 2/2010 | Manley |
| 2010/0030210 A1 | 2/2010 | Paulus |
| 2010/0045558 A1 | 2/2010 | Rossetto |
| 2010/0045559 A1 | 2/2010 | Rossetto |
| 2010/0057070 A1 | 3/2010 | Behnke et al. |
| 2010/0076422 A1 | 3/2010 | Podhajsky |
| 2010/0087808 A1 | 4/2010 | Paulus |
| 2010/0094272 A1 | 4/2010 | Rossetto et al. |
| 2010/0094273 A1 | 4/2010 | Rossetto et al. |
| 2010/0097284 A1 | 4/2010 | Brannan et al. |
| 2010/0217252 A1* | 8/2010 | Rossetto ............. A61B 18/18 606/33 |
| 2010/0256624 A1 | 10/2010 | Brannan et al. |
| 2010/0262134 A1 | 10/2010 | Jensen et al. |
| 2010/0286681 A1 | 11/2010 | Podhajsky |
| 2010/0286682 A1 | 11/2010 | Podhajsky |
| 2010/0286683 A1 | 11/2010 | Podhajsky |
| 2010/0305560 A1 | 12/2010 | Peterson |
| 2011/0196362 A1 | 8/2011 | Rossetto |

FOREIGN PATENT DOCUMENTS

| | | |
|---|---|---|
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10328514 B3 | 3/2005 |
| DE | 102004022206 A1 | 12/2005 |
| DE | 202005015147 U1 | 2/2006 |
| EP | 246350 A1 | 11/1987 |
| EP | 0481685 A1 | 4/1992 |
| EP | 0521264 A2 | 1/1993 |
| EP | 556705 A1 | 8/1993 |
| EP | 0558429 A1 | 9/1993 |
| EP | 0572131 A1 | 12/1993 |
| EP | 0541930 B1 | 3/1998 |
| EP | 836868 A2 | 4/1998 |

(56) References Cited

FOREIGN PATENT DOCUMENTS

| | | | |
|---|---|---|---|
| EP | 1186274 A2 | 3/2002 | |
| EP | 1159926 A3 | 3/2003 | |
| EP | 2221921 A1 | 8/2010 | |
| FR | 179 607 | 11/1906 | |
| FR | 1 275 415 A | 11/1961 | |
| FR | 1 347 865 A | 1/1964 | |
| FR | 2 235 669 A1 | 1/1975 | |
| FR | 2 276 027 A1 | 1/1976 | |
| FR | 2 313 708 A1 | 12/1976 | |
| FR | 2 502 935 A1 | 10/1982 | |
| FR | 2 517 953 A1 | 6/1983 | |
| FR | 2 573 301 A1 | 5/1986 | |
| FR | 2 862 813 A1 | 5/2005 | |
| FR | 2 864 439 A1 | 7/2005 | |
| JP | 55106 | 1/1993 | |
| JP | 0540112 | 2/1993 | |
| JP | 06343644 A | 12/1994 | |
| JP | 07265328 A | 10/1995 | |
| JP | 08056955 A | 3/1996 | |
| JP | 08252263 A | 10/1996 | |
| JP | 09010223 A | 1/1997 | |
| JP | 11244298 A | 9/1999 | |
| JP | 2000342599 A | 12/2000 | |
| JP | 2000350732 A | 12/2000 | |
| JP | 20018944 | 1/2001 | |
| JP | 200129356 | 2/2001 | |
| JP | 2001128990 A | 5/2001 | |
| SU | 166452 | 1/1965 | |
| SU | 401367 A1 | 10/1973 | |
| SU | 727201 A2 | 4/1980 | |
| WO | 2004084748 A1 | 10/2004 | |
| WO | 2006084676 A1 | 8/2006 | |
| WO | WO-2006084676 A1 * | 8/2006 | ............. A61B 18/18 |

OTHER PUBLICATIONS

European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: Targis.TM. Technology (Date Unknown). "Overcoming the Challenge" located at: <http://www.urologix.com!medicaUtechnology.html > Nov. 18, 1999: 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Elcctosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
European Search Report dated Oct. 9, 2013 in European Application No. 13004127.
U.S. Appl. No. 08/483,742, filed Jun. 7, 1995.
U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.

(56) References Cited

OTHER PUBLICATIONS

U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
International Search Report PCT/US03/37110 dated Jul. 25, 2005.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas MedicalCenter,Charlotte, NC 2003.
Esterline Product Literature, "Light Key: Visualize a Virtual Keyboard. One With no. Moving Parts", 4 pages.
Esterline, "Light Key Projection Keyboard" 2004 Advanced Input Systems, located at: <http://www.advanced-input.com/lightkey> last visited on Feb. 10, 2005.
Goldberg et al., "Image-guided Radiofrequency Tumor Ablation: Challenges and Opportunities—Part I", (2001) J Vasc. Interv. Radiol, vol. 12, pp. 1021-1032.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Paul G. Horgan, "A Novel Technique for Parenchymal Division During Hepatectomy" The American Journal of Surgery, vol. 181, No. 3, OApr. 2001, pp. 236-237.
Sugita et al., "Bipolar Coagulator with Automatic Thermocontrol" J. Neurosurg., vol. 41, Dec. 1944, pp. 777-779.
S. Humphries Jr. et al., "Finite Element Codes to Model Electrical Heating and Non.cndot.LInear Thermal Transport in Biological Media", Proc. ASME HTD-355, 131 (1997).
Urologix, Inc.—Medical Professionals: Targis.TM. Technology (Date Unknown). "Overcoming the Challenge" located at: <http://www.urologix.com!medicaUtechnology.html > last visited on Apr. 27, 2001, 3 pages.
ValleyLab Brochure, "Electosurgery: A Historical Overview", Innovations in Electrosurgery, 1999.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Intl Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences.cndot.Yingyong Kexue Xuebao, Shangha CN, vol. 23, No. 2:(2005.cndot.03): pp. 160-184.
Ogden, "Goertzel Alternative to the Fourier Transform" Jun. 1993 pp. 485-487 Electronics World: Reed Business Publishing, Sutton, Surrey, BG, vol. 99, No. 9, 1687.
Olsson M.D. et al., "Radical Cystectomy in Females" Current Surgical Techniques in Urology. vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al, "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure. "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Intl Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Nestrosurg., vol. 41, Dec. 1944, pp. 777-779.
LigaSure.TM. Vessel Sealing System, the Seal of Confidence in General , Gynecologic, Urologic, and Laparaoscopic Surgery, Sales/ Product Literature, Jan. 2004.
European Search Report EP 06024123.9 dated Mar. 6, 2007.
European Search Report EP 06025700.3 dated Apr. 12, 2007.
European Search Report EP 07000885.9 dated May 15, 2007.

(56) References Cited

OTHER PUBLICATIONS

European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 10005533 dated Sep. 24, 2010.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
Australian Examination Report issued in Appl. No. 2015264779 dated Jul. 3, 2017.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
Canadian Office Action from Appl. No. 2,706,194 dated Dec. 17, 2015 (8 pages).
U.S. Appl. No. 08/843,742, filed Jun. 7, 1995, Roger A. Stern.
U.S. Appl. No. 08/136,098, filed Oct. 14, 1993, Roger A. Stern.

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic .RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSuren.TM. Device in the Hemostasis of Small, Medium, and Large-Sized Arteries" Carolinas Laparoscopic and Advanced Surgery Program, Carolinas MedicalCenter,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw.cndot.Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.

(56) References Cited

OTHER PUBLICATIONS

Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI. Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Goldberg et al., "Image-guided Radiofrequency Tumor Ablation: Challenges and Opportunities—Part 1", (2001) J Vasc. Interv. Radiol, vol. 12, pp. 1021-1032.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands. vol. 4; No. 1. pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure.TM. Vessel Sealing System for Peri-Hilar Vessels in Laparoscopic Nephrectomy" Sales/Product Literature 2000.
Johnson, "Evaluation of the LigaSure.TM. Vessel Sealing System in Hemorrhoidectormy" American College of Surgeons (ACS) Clinic La Congress Poster (2000).
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12:876-878.
K. Ogata, Modern Control Engineering, Prentice-Hall, Englewood Cliffs, N.J., 1970.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.

* cited by examiner

ELECTROSURGICAL DEVICES WITH DIRECTIONAL RADIATION PATTERN

CROSS-REFERENCE TO RELATED APPLICATIONS

This application is a Continuation of U.S. patent application Ser. No. 14/242,048, filed on Apr. 1, 2014, which is a Divisional of U.S. patent application Ser. No. 13/567,624, filed on Aug. 6, 2012, now U.S. Pat. No. 8,690,869, which is a Continuation of U.S. patent application Ser. No. 12/476,960, filed on Jun. 2, 2009, now U.S. Pat. No. 8,235,981, the entire contents of each of which is incorporated by reference herein.

BACKGROUND

1. Technical Field

The present disclosure relates to electrosurgical devices suitable for use in tissue ablation applications and, more particularly, to electrosurgical devices with directional radiation patterns.

2. Discussion of Related Art

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction may occur. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator, which functions as an energy source, and a microwave surgical instrument (e.g., microwave ablation probe) having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

There are several types of microwave antenna assemblies for the ablation of tissue, such as monopole, dipole and helical. In monopole and dipole antenna assemblies, microwave energy radiates perpendicularly away from the axis of the conductor. Monopole antenna assemblies include a single elongated conductor whereas a typical dipole antenna assembly includes two elongated conductors, which are linearly aligned and positioned end-to-end relative to one another with an electrical insulator placed therebetween. Helical antenna assemblies include a helically-shaped conductor connected to a ground plane. Helical antenna assemblies can operate in a number of modes, such as normal mode (broadside), in which the field radiated by the helix is maximum in a perpendicular plane to the helix axis, and axial mode (end fire), in which maximum radiation is along the helix axis.

A microwave transmission line typically includes a long, thin inner conductor that extends along a longitudinal transmission line axis and surrounded by a dielectric material and is further surrounded by an outer conductor around the dielectric material such that the outer conductor also extends along the transmission line axis. In one variation of an antenna, a length of transmission line is provided with a plurality of openings through which energy "leaks" or radiates away from the transmission line or coaxial cable. This type of construction is typically referred to as a "leaky coaxial" or "leaky wave" antenna. A leaky wave antenna is basically a waveguiding structure constructed so as to "leak" power along the length of the guiding structure.

During certain procedures, it can be difficult to assess the extent to which the microwave energy will radiate into the surrounding tissue, making it difficult to determine the area or volume of surrounding tissue that will be ablated.

SUMMARY

The present disclosure relates to a device for directing energy to a target volume of tissue including an antenna assembly and an elongated body member. The elongated body member includes a proximal end portion and a distal end portion, wherein the proximal and distal end portions define a longitudinal axis, the elongated body member having a body wall defining a chamber therein. The antenna assembly is disposed in the chamber. The elongated body member also includes an opening in the body wall to allow energy radiated from the antenna assembly to transfer into the target volume of tissue.

The present disclosure also relates to an ablation applicator including a catheter assembly and an antenna assembly. The catheter assembly includes a tubular body member having an outer surface. The outer surface of the tubular body member includes an aperture formed therethrough. At least one of the catheter assembly and the outer surface of the tubular body member is formed of an electrically conductive material. The antenna assembly is disposed in the tubular body member of the catheter assembly. The aperture in the outer surface of the tubular body member is configured to allow energy to radiate from the antenna assembly in a directional broadside radiation pattern.

The present disclosure also relates to a method for directing energy to a target volume of tissue including the steps of providing a device including an elongated body member having a body wall defining a chamber therein, and an antenna assembly disposed in the chamber, wherein the elongated body member includes an opening in the body wall, and positioning the device to the target volume of tissue. The method also includes the steps of transmitting energy from an energy source to the antenna assembly, and causing the energy to radiate through the opening in a broadside radiation pattern to the target volume of tissue.

BRIEF DESCRIPTION OF THE DRAWINGS

Objects and features of the presently disclosed antenna assemblies will become apparent to those of ordinary skill in the art when descriptions of various embodiments thereof are read with reference to the accompanying drawings, of which.

DETAILED DESCRIPTION

Hereinafter, embodiments of the presently disclosed electrosurgical device with a directional radiation pattern will be described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus that is closer to the user and the term "distal" refers to that portion of the apparatus that is further from the user.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as microwave ablation or microwave ablation assisted resection. As it is used in this description, "transmission line" generally refers to any transmission medium that can be used for the propagation of signals from one point to another.

Various embodiments of the present disclosure provide electrosurgical devices for treating tissue and methods of directing electromagnetic radiation to a target volume of tissue. Embodiments may be implemented using electromagnetic radiation at microwave frequencies or at other frequencies. An electrosurgical system including an energy applicator, according to various embodiments, is designed and configured to operate between about 500 MHz and about 10 GHz with a directional radiation pattern.

Various embodiments of the presently disclosed electrosurgical device with a directional radiation pattern are suitable for microwave ablation and for use to pre-coagulate tissue for microwave ablation assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue. In addition, although the following description describes the use of a dipole microwave antenna, the teachings of the present disclosure may also apply to a monopole, helical, or other suitable type of microwave antenna.

Figure 1:
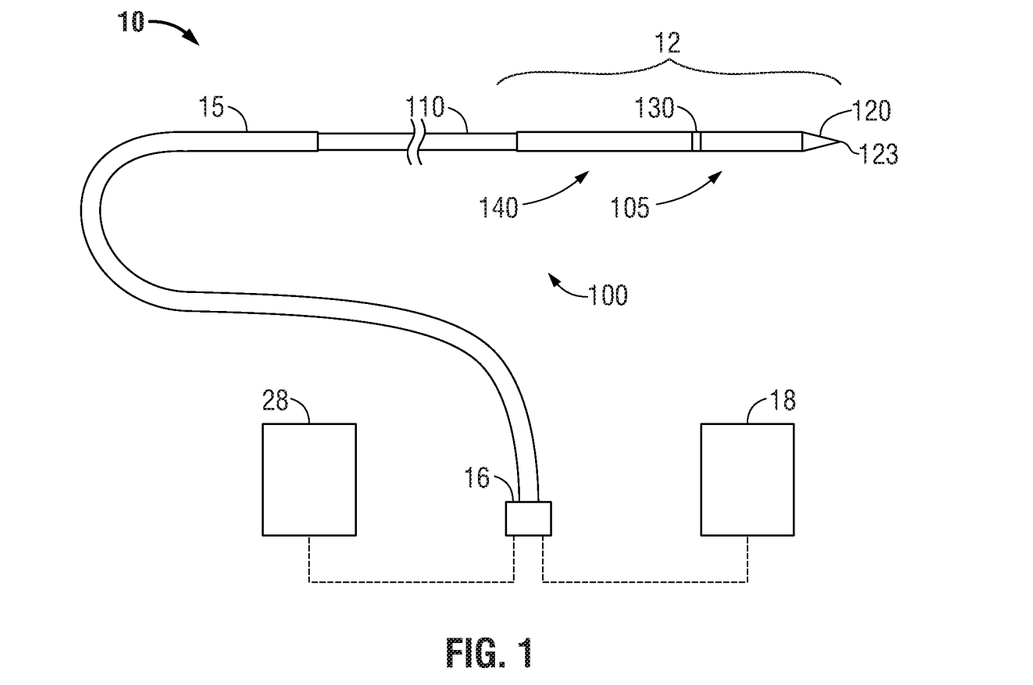
FIG. 1 is a schematic diagram of an ablation system according to an embodiment of the present disclosure.

FIG. 1 shows an electrosurgical system 10, according to an embodiment of the present disclosure, which includes an energy applicator or probe 100. Energy applicator 100 includes an antenna assembly 12 that is connected by a feedline 110 (or shaft) via a transmission line 15 to a connector 16, which may further operably connect the probe 100 to a power generating source 28, e.g., a microwave or radio frequency (RF) electrosurgical generator. In some embodiments, the power generating source 28 is configured to provide microwave energy at an operational frequency from about 500 MHz to about 2500 MHz. In other embodiments, the power generating source 28 is configured to provide microwave energy at an operational frequency from about 500 MHz to about 10 GHz. Power generating source 28 may be configured to provide various frequencies of electromagnetic energy. Transmission line 15 may additionally or alternatively provide a conduit (not shown) configured to provide coolant from a coolant source 18 to the probe 100.

Located at the distal end of the antenna assembly 12 is an end cap or tapered region 120, which may terminate in a sharp tip 123 to allow for insertion into tissue with minimal resistance. One example of a straight probe with a sharp tip that may be suitable for use as the energy applicator 100 is commercially available under the trademark Evident™ offered by Covidien. The end cap portion or tapered region 120 may include other shapes, such as, for example, a tip 123 that is rounded, flat, square, hexagonal, or cylindroconical.

In some variations, the antenna assembly 12 includes a distal radiating portion 105 and a proximal radiating portion 140. A feedpoint or puck 130 may be provided. In some embodiments, the puck 130, having length "L2", is a junction member that couples the proximal radiating portion 140 and the distal radiating portion 105. Puck 130, or portions thereof, may be disposed between the proximal and distal radiating portions, 140 and 105. Puck 130 may be formed from any suitable elastomeric or ceramic dielectric material by any suitable process. In some embodiments, the puck 130 is formed by overmolding and includes a thermoplastic elastomer, such as, for example, polyether block amide (e.g., PEBAX®, manufactured by The Arkema Group of Colombes, France), polyetherimide (e.g., ULTEM® and/or EXTEM®, manufactured by SABIC Innovative Plastics of Saudi Arabia) and/or polyimide-based polymer (e.g., VES-PEL®, manufactured by E. I. du Pont de Nemours and Company of Wilmington, Del., United States). Puck 130 may be formed using any suitable overmolding compound by any suitable process, and may include use of a ceramic substrate.

In some embodiments, the antenna assembly 12 may be provided with a coolant chamber (not shown). Additionally, the puck 130 may include coolant inflow and outflow ports (not shown) to facilitate the flow of coolant into, and out of, the coolant chamber. Examples of coolant chamber and coolant inflow and outflow port embodiments are disclosed in commonly assigned U.S. patent application Ser. No. 12/401,268 filed on Mar. 10, 2009, entitled "COOLED DIELECTRICALLY BUFFERED MICROWAVE DIPOLE ANTENNA", and U.S. Pat. No. 7,311,703, entitled "DEVICES AND METHODS FOR COOLING MICROWAVE ANTENNAS".

In some embodiments, the antenna assembly 12 may be provided with an outer jacket (not shown) disposed about the distal radiating portion 105, the puck 130 and/or the proximal radiating portion 140. The outer jacket may be formed of any suitable material, such as, for example, polymeric or ceramic materials. The outer jacket may be applied by any suitable method, such as, for example, heat shrinking, overmolding, coating, spraying dipping, powder coating, baking and/or film deposition.

During microwave ablation, e.g., using the electrosurgical system 10, the probe 100 is inserted into or placed adjacent to tissue and microwave energy is supplied thereto. Ultrasound or computed tomography (CT) guidance may be used to accurately guide the probe 100 into the area of tissue to be treated. Probe 100 may be placed percutaneously or surgically, e.g., using conventional surgical techniques by surgical staff. A clinician may pre-determine the length of time that microwave energy is to be applied. Application duration may depend on many factors such as tumor size and location and whether the tumor was a secondary or primary cancer. The duration of microwave energy application using the probe 100 may depend on the progress of the heat distribution within the tissue area that is to be destroyed and/or the surrounding tissue. Single or multiple probes 100 may provide ablations in short procedure times, e.g., a few minutes, to destroy cancerous cells in the target tissue region.

A plurality of probes 100 may be placed in variously arranged configurations to substantially simultaneously ablate a target tissue region, making faster procedures possible. Multiple probes 100 can be used to synergistically create a large ablation or to ablate separate sites simultaneously. Tissue ablation size and geometry is influenced by a variety of factors, such as the energy applicator design, number of energy applicators used simultaneously, time and wattage.

Figure 2:
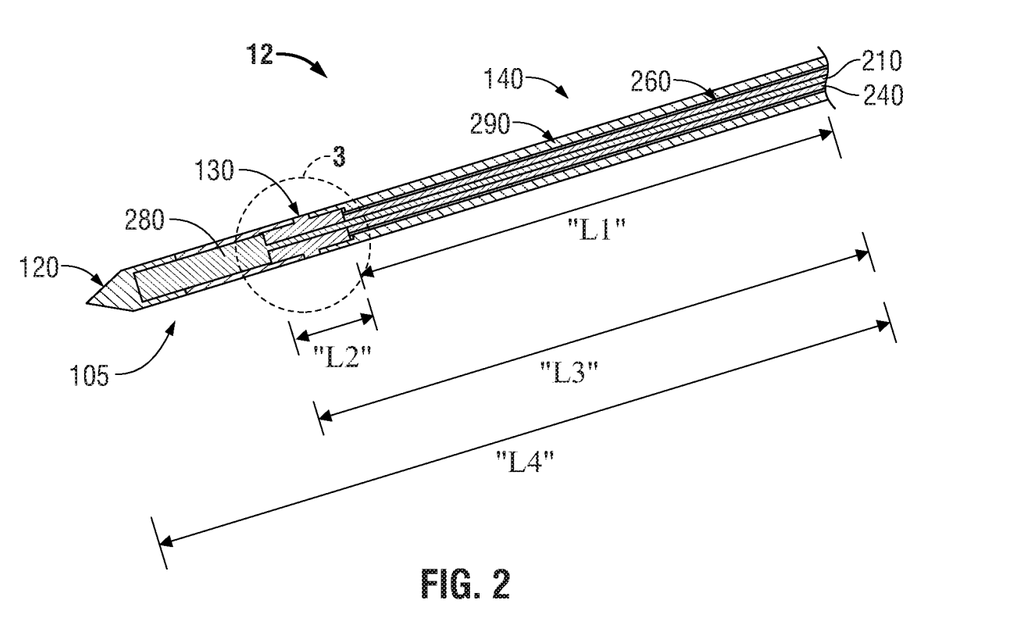
FIG. 2 is a partial, longitudinal cross-sectional view of an energy applicator of the ablation system shown in FIG. 1 according to an embodiment of the present disclosure.
Figure 3:
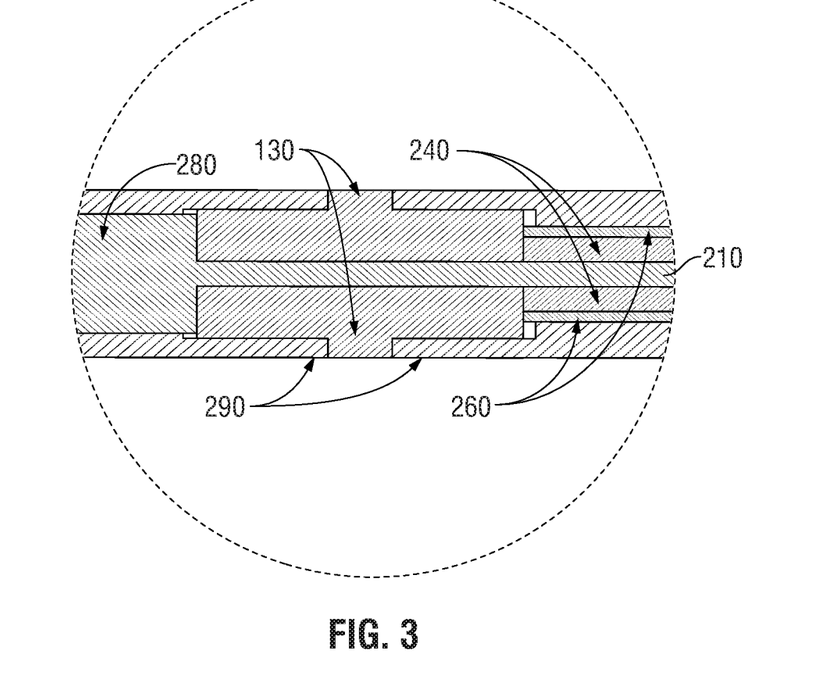
FIG. 3 is an enlarged view of the indicated area of detail of FIG. 2 according to an embodiment of the present disclosure.

Referring to FIGS. 2 and 3, an embodiment of the antenna assembly 12 of FIG. 1 is shown and includes an inner conductor 210, having length "L3", an outer conductor 260, having length "L1", and may include a first dielectric material 240 separating the inner conductor 210 and the outer conductor 260. In some embodiments, the inner conductor 210 is formed from a first electrically conductive material (e.g., stainless steel) and the outer conductor 260 is formed from a second electrically conductive material (e.g., copper). In some embodiments, the outer conductor 260 coaxially surrounds the inner conductor 210 along a distal portion of the antenna assembly 12, having length "L1", as shown in FIG. 2. Inner conductor 210 and the outer conductor 260 may be formed from any suitable electrically conductive material.

First dielectric material 240 may be formed from any suitable dielectric material, including, but not limited to, ceramics, water, mica, polyethylene, polyethylene terephthalate, polyimide, polytetrafluoroethylene (PTFE) (e.g., Teflon®, manufactured by E. I. du Pont de Nemours and Company of Wilmington, Del., United States), glass, or metal oxides. Antenna assembly 12 may be provided with a second dielectric material 290 surrounding the outer conductor 260 and/or the puck 130, or portions thereof. Second dielectric material 290 may be formed from any suitable dielectric material. In some embodiments, the second dielectric material 290 is formed from a material with a dielectric constant different than the dielectric constant of the first dielectric material 240.

In some embodiments, the antenna assembly 12, having length "L4", includes a conductor end portion 280, which may be formed from any suitable electrically conductive material. In some embodiments, the conductor end portion 280 is coupled to the inner conductor 210 and may be formed of the same material as the inner conductor 210. As shown in FIG. 2, the conductor end portion 280 may be spaced apart a length "L2" from the outer conductor 260 by the puck 130, having length "L2", disposed therebetween. Tapered region 120, or portions thereof, may surround a proximal portion of the conductor end portion 280. In some embodiments, the conductor end portion 280 is substantially cylindrically shaped, and may be formed from stainless steel. The shape and size of the conductor end portion 280 may be varied from the configuration depicted in FIG. 2. In some embodiments, at least a portion of the conductor end portion 280 is surrounded by the second dielectric material 290.

Figure 4:
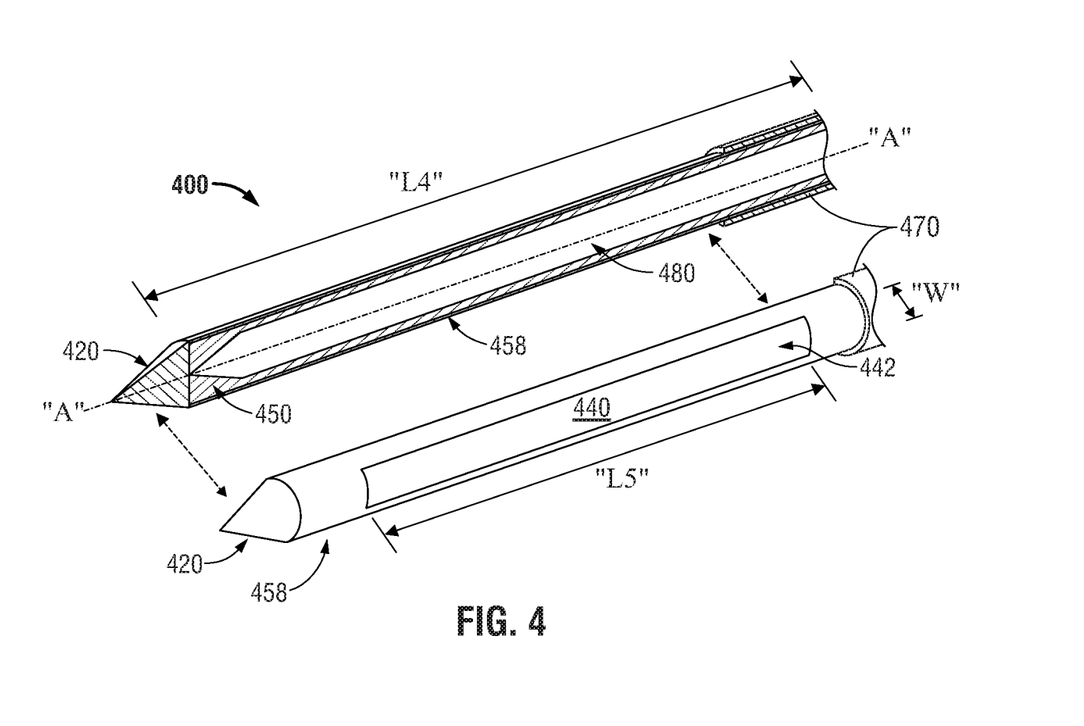
FIG. 4 is a partial, longitudinal cross-sectional (split) view of an elongated body member configured to receive the energy applicator of FIG. 2 according to an embodiment of the present disclosure.
Figure 5:
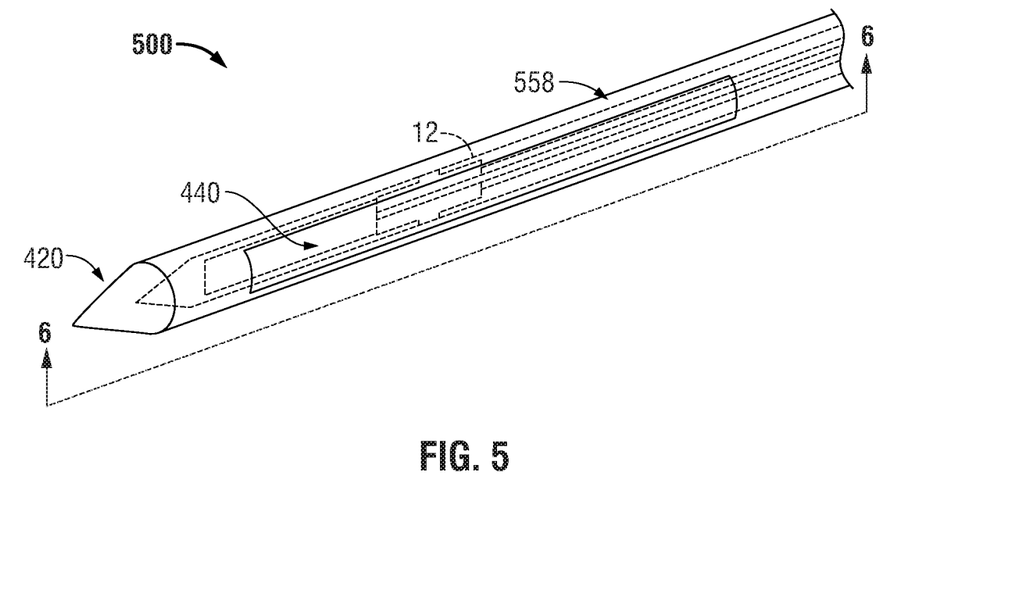
FIG. 5 is a partial, perspective view of an electrosurgical device including the elongated body member of FIG. 4 shown with the energy applicator of FIG. 2 (in phantom lines) disposed therein according to an embodiment of the present disclosure.
Figure 6:
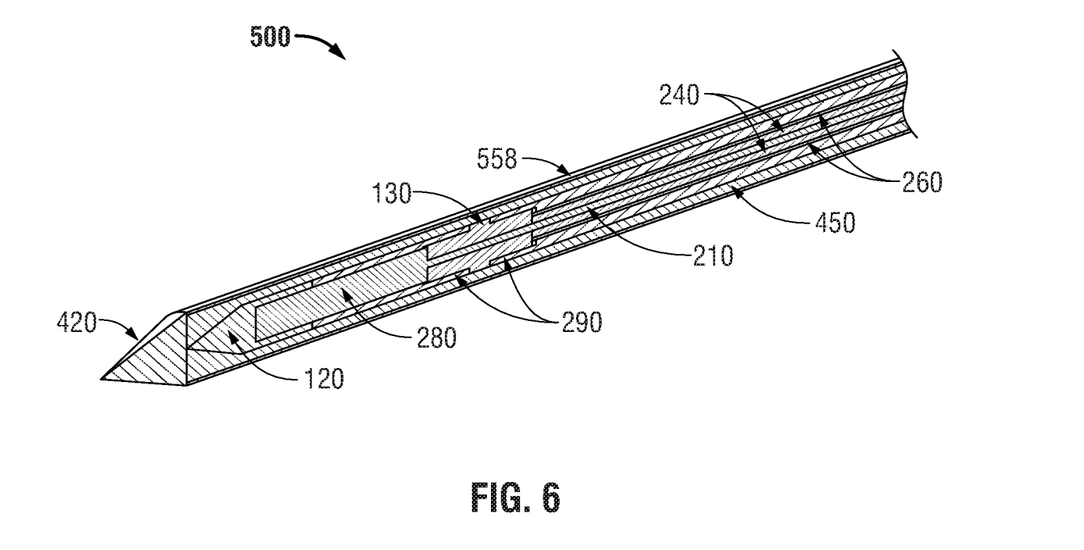
FIG. 6 is partial, longitudinal cross-sectional view of the electrosurgical device of FIG. 5 according to an embodiment of the present disclosure.

FIG. 4 shows an elongated body member 400, according to an embodiment of the present disclosure, which is configured to receive an energy applicator (e.g., 100 shown in FIG. 1), or portions thereof. An electrosurgical device that includes the elongated body member 400 is shown in FIGS. 5 and 6. In some embodiments, the elongated body member 400 is substantially tubular, except for a tapered portion 420 tapering from the distal end thereof. Tapered portion 420 may include a tip portion, which may be advantageously configured to facilitate penetration of tissue. Although the surfaces of the tapered portion 420 shown in FIGS. 4 through 6 are generally flat, the surfaces of the tapered portion 420 according to various embodiments may be curved or may include a combination of flat, sloped or curved portions. The shape and size of the tapered portion 420 may be varied from the configuration depicted in FIGS. 4 through 6.

Elongated body member 400 includes a proximal end portion, a distal end portion, wherein the proximal and distal end portions define a longitudinal axis "A-A", a chamber 480 surrounding and extending along the axis "A-A", and a body wall 450 surrounding the chamber 480. Chamber 480 is configured to receive at least a portion of an energy applicator (e.g., 100 shown in FIG. 1). In some embodiments, the chamber 480 is dimensioned and configured to receive an antenna assembly (e.g., 12 shown in FIGS. 5 and 6) within the chamber 480. The shape and size of the chamber 480 may be varied from the configuration depicted in FIGS. 5 and 6.

Figure 7:
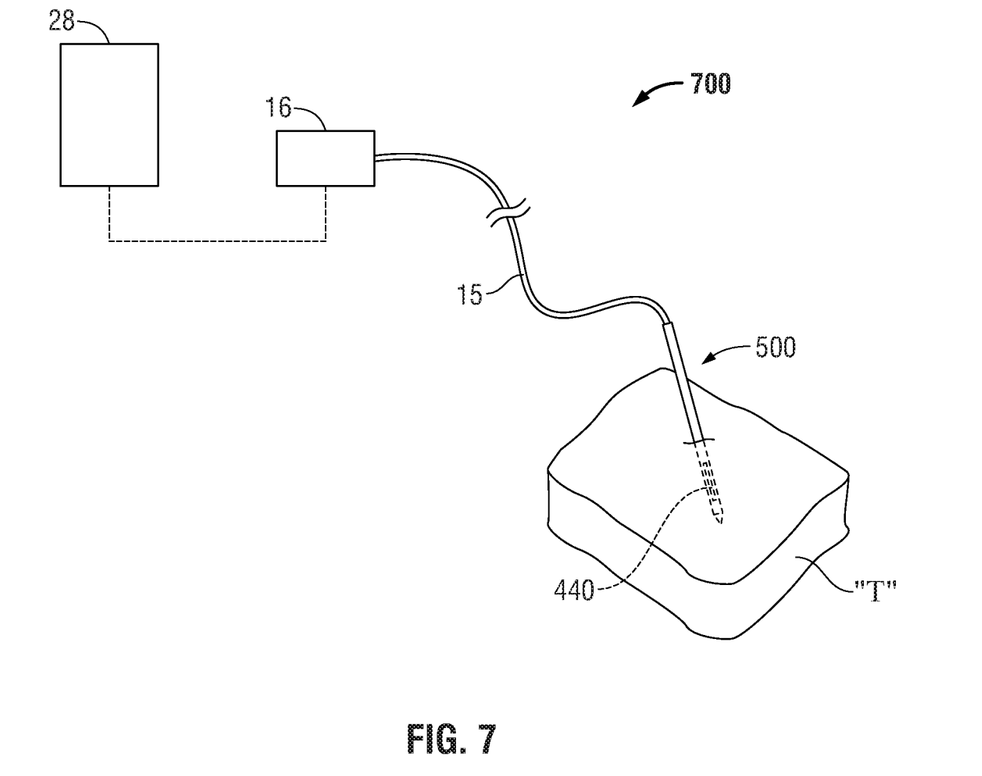
FIG. 7 is a schematic diagram of an ablation system including the electrosurgical device of FIGS. 5 and 6 according to an embodiment of the present disclosure.

Body wall 450 is provided with at least one opening 440 therethough to allow electromagnetic energy radiated from the energy applicator to transfer into the target volume of tissue (e.g., "T" shown in FIG. 7). In some embodiments, the opening 440 is configured for radiating energy in a broadside radiation pattern, such as the non-limiting example directional radiation patterns shown in FIGS. 9 and 10. As shown in FIGS. 4 and 5, a substantially slot-shaped opening 440, having length "L5" and width "W", may be positioned at a side portion of the body wall 450, and may have a longitudinal axis that extends substantially parallel to the axis "A-A". The shape and size of the opening 440 may be varied from the configuration depicted in FIGS. 4 and 5.

Elongated body member 400 may include a plurality of openings 440. In some embodiments, the body wall 450 is provided with a plurality of elongated slots, which may be spaced longitudinally along the elongated body member 400. The size, shape and/or location of each opening 440 may be based on the wavelength of the radiated energy along the antenna radiating portion (e.g., 140 and/or 105 shown in FIG. 2). The number of openings 440 may be based on various factors, such as, for example, the volume of target tissue to be treated, the desired procedure, the wavelength of the electromagnetic energy to be radiated, and the shape and/or dimensions of the openings. The size and/or shape of each opening 440 may be based on the location of the opening 440 relative to a distal tip of the antenna assembly 12. In some embodiments, the antenna assembly 12 is a dipole antenna, and the openings 440 may be configured to encompass any radial angle, length, and positioning with respect to the antenna dipole arms.

Opening 440 may be provided with an electrically nonconductive material 442. Nonconductive material 442 may include a nonconductive RF transparent material, e.g., a glass fiber epoxy composite or polyimide. In some embodiments, the nonconductive material 442 substantially entirely fills the recess or void formed by the opening 440 in the elongated body member 400. Opening 440 may be filled with the nonconductive material 442 such that the external surface of the elongated body member 400 is substantially smooth.

Elongated body member 400 may include an outer jacket (e.g., 458 shown in FIG. 4 or 558 shown in FIGS. 5 and 6). Outer jacket 458 may be formed of any suitable electrically conductive material, such as, for example, electrically conducting metallic ceramic and polymeric electrically conductive materials. Outer jacket 458 may include metal and/or conductive oxide layers. Outer jacket 458 may be configured to surround the body wall 450, or portions thereof, and/or the tapered portion 420, or portions thereof. In some embodiments, the outer jacket 458 is formed of an electrically conductive material and configured to substantially surround the body wall 450, except for the opening 440 and the electrically nonconductive material 442 disposed therein.

Elongated body member 400 may be a tubular body (e.g., a tubular body member of a catheter assembly) having an outer surface (e.g., 458 shown in FIGS. 5 and 6) that includes a single or multiple openings 440 formed therethrough. In some embodiments, the tubular body member is formed of an electrically conductive material and/or the outer surface of the tubular body member is formed of an electrically conductive material.

FIGS. 5 through 7 show an electrosurgical device 500, according to an embodiment of the present disclosure, which is configured to operate with a directional radiation pattern. Electrosurgical device 500 includes the elongated body member 400 of FIG. 4 and the antenna assembly 12 of FIG. 2 disposed within the chamber 480 of the elongated body member 400. Antenna assembly 12 and the elongated body member 400 may be disengageably coupled to each other. Electrosurgical device 500 may be sufficiently small in diameter to be minimally invasive of the body, which may reduce the preparation time of the patient as might be required for more invasive penetration of the body.

Electrosurgical device 500 may include a moveable sleeve member 470 (FIG. 4) associated with elongated body member 400 and coaxially aligned with the axis "A-A". Such a sleeve member 470 may either be on the outside or the inside of elongated body member. In some embodiments, the sleeve member 470 may be adapted to be rotationably moveable and/or slideably moveable along the outside of the antenna assembly 12 to various axial positions or various rotational positions to vary the size of the opening 440 with rotation angle. The sleeve member 470 may include a plurality of apertures and may be moveable relative to the elongated body member 400 to various positions, thereby providing variably dimensioned electromagnetic "windows" within the opening 440. In other embodiments, the elongated body member 400 itself may be adapted to be rotationably moveable and/or slideably moveable along the outside of the antenna assembly 12.

FIG. 7 shows an electrosurgical system 700, according to an embodiment of the present disclosure, which includes the electrosurgical device 500 of FIGS. 5 and 6. Electrosurgical device 500 is coupled to a connector 16 via a transmission line 15, which may further connect the electrosurgical device 500 to a power generating source 28, e.g., a microwave or RF electrosurgical generator. During a procedure, e.g., an ablation, the electrosurgical device 500 of the electrosurgical system 700 is inserted into or placed adjacent to tissue "T" and energy is supplied thereto. Electrosurgical device 500 may be placed percutaneously or surgically. Ultrasound or computed tomography (CT) guidance may be used to accurately guide the electrosurgical device 500 into the area of tissue "T" to be treated.

Figure 8:
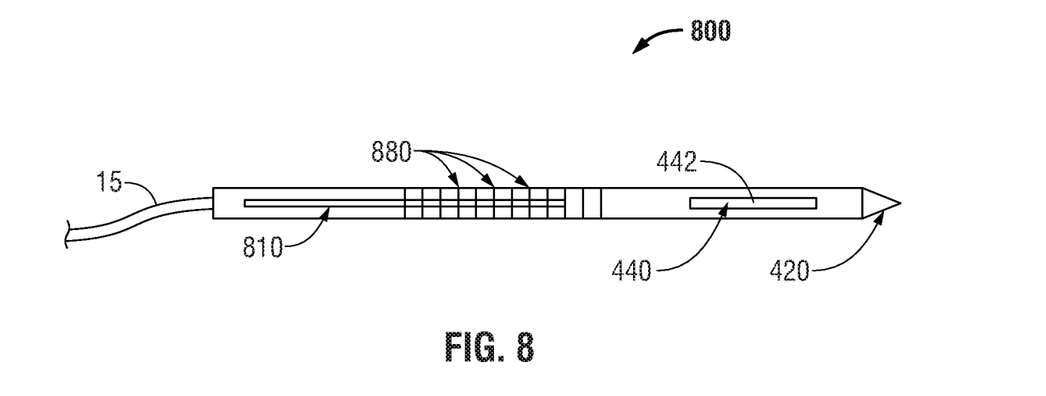
FIG. 8 is a schematic diagram of the electrosurgical device of FIGS. 5 through 7 shown with indicia graduation marks and an indicia alignment mark according to an embodiment of the present disclosure.

FIG. 8 shows an electrosurgical device 800, which is similar to the electrosurgical device 500 of FIGS. 5 through 7, except for the indicia alignment mark 810 and the indicia graduation marks 880 on the proximal end of the electrosurgical device 800. Indicia alignment mark 810 and/or the indicia graduation marks 880 may be carried on or inscribed into the elongated body member of the electrosurgical device 800. In some embodiments, the electrosurgical device 800 includes a plurality of indicia graduation marks 880 defining units of linear measure, which may be inscribed substantially circumferentially about the elongated body member. Indicia graduation marks 880 may be used to indicate the relative position of the opening 440 with respect to the surface of the tissue "T". In some embodiments, the indicia graduation marks 880 are used to indicate the position of the distal end of the opening 440 relative to the surface of the tissue "T". Indicia graduation marks 880 may be arranged to form an incremental pattern using any standard measure of length, e.g., inches or centimeters.

In some embodiments, the electrosurgical device 800 includes an indicia alignment mark 810, e.g., a colored stripe, which is readily visible along the proximal end of the elongated body member. Indicia alignment mark 810 is positioned on the elongated body member such that the longitudinal axis of the alignment mark 810 substantially aligns with the longitudinal axis of the opening 440, to provide a visual cue to the surgeon to allow orientation of the direction of flow of the energy to coincide with the indicia alignment mark 810. As shown in FIG. 8, one or more of the indicia graduation marks 880 may overlap the indicia alignment mark 810. The shape and size of the indicia alignment mark 810 and the indicia graduation marks 880 may be varied from the configurations depicted in FIG. 8.

Figure 9:
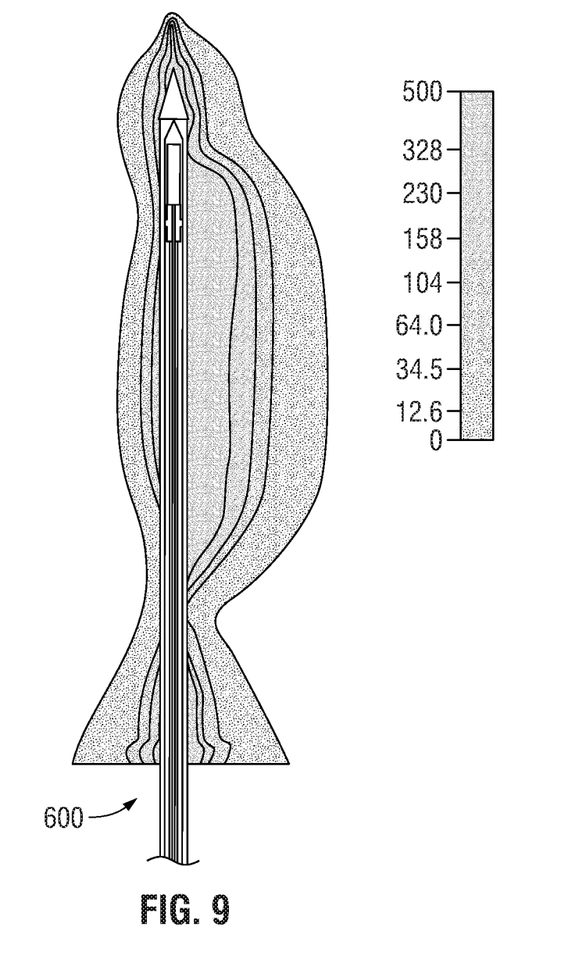
FIGS. 9 and 10 are schematically-illustrated representations of simulation results showing broadside radiation patterns according to embodiments of the present disclosure.
Figure 10:
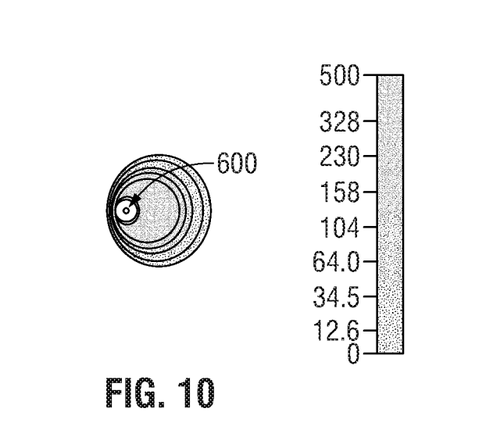

FIGS. 9 and 10 are schematically-illustrated representations of simulation results showing directional radiation patterns. The illustrated results are based on a simulation that modeled operation of an electrosurgical device 600, which is configured to operate with a directional radiation pattern. Electrosurgical device 600 shown in FIGS. 9 and 10 is similar to the electrosurgical device 500 of FIGS. 5 through 7 and further description thereof is omitted in the interests of brevity.

Figure 11:
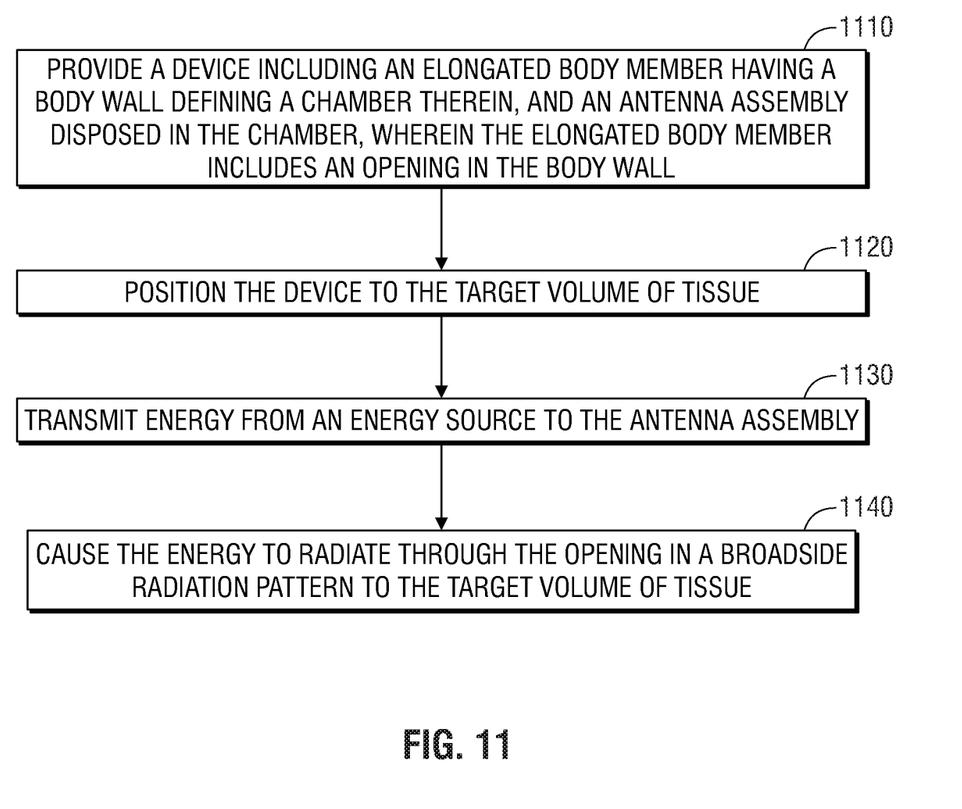
FIG. 11 is a flowchart illustrating a method of directing energy to a target volume of tissue according to an embodiment of the present disclosure.

FIG. 11 is a flowchart illustrating a method of directing energy to a target volume of tissue, according to an embodiment of the present disclosure. In step 1110, an electrosurgical device (e.g., 500 shown in FIGS. 5 through 7) is provided, wherein the device includes an elongated body member (e.g., 400 shown in FIG. 4) having a body wall defining a chamber therein, and an antenna assembly disposed in the chamber, wherein the elongated body member includes an opening (e.g., 440 shown in FIG. 7) in the body wall.

In step 1120, the device is positioned to the target volume of tissue. The electrosurgical device may be inserted directly into tissue (e.g., "T" shown in FIG. 7), inserted through a lumen, e.g., a vein, needle or catheter, placed into the body during surgery by a clinician, or positioned in the body by other suitable methods known in the art. The electrosurgical device is configured to operate with a directional radiation pattern. In some embodiments, the electrosurgical device is configured to operate with a broadside radiation pattern. In other embodiments, the catheter or needle contains the opening to allow a directional radiation pattern.

In step 1130, energy from an energy source (e.g., 28 shown in FIG. 7) is transmitted to the antenna assembly. For example, the energy source may be any suitable electrosurgical generator for generating an output signal. In some embodiments, the energy source is a microwave energy source, and may be configured to provide microwave energy at an operational frequency from about 500 MHz to about 10 GHz.

In step 1140, the energy from the energy source is caused to radiate through the opening in the elongated body member. In some embodiments, the opening is configured for radiating energy in a broadside radiation pattern.

The above-described electrosurgical devices for treating tissue and methods of directing electromagnetic radiation to a target volume of tissue may be used to provide directional microwave ablation, wherein the heating zone may be focused to one side of the electrosurgical device, thereby allowing clinicians to target small and/or hard tumors without having to penetrate the tumor directly or kill more healthy tissue than necessary. The presently disclosed electrosurgical devices may allow clinicians to avoid ablating critical structures, such as large vessels, healthy organs or vital membrane barriers, by placing the electrosurgical device between the tumor and critical structure and directing the electromagnetic radiation toward the tumor and away from the critical structure.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure. For example, with reference to FIGS. 4 and 5, the electrosurgical device 500 may be rotatable about axis "A-A" such that the directional radiation pattern rotates therewith.

What is claimed is:

1. An electrosurgical device for treating tissue, the electrosurgical device comprising:
   an elongated body member defining a chamber therein and having a body wall, the body wall having an opening defined therethrough, the elongated body member including an electrically conductive outer jacket disposed on the body wall;
   an antenna assembly disposed in the chamber and configured to deliver electrosurgical energy to tissue; and
   an outer sleeve disposed about the elongated body member, at least one of the elongated body member or the outer sleeve movable relative to the other to control exposure of the opening of the body wall.

2. The electrosurgical device of claim 1, wherein the outer sleeve is longitudinally slidable along a longitudinal axis defined by the elongated body member.

3. The electrosurgical device of claim 1, wherein the outer sleeve is rotatable about a longitudinal axis defined by the elongated body member.

4. The electrosurgical device of claim 1, wherein the outer sleeve is configured to control an amount of the electrosurgical energy delivered from the antenna assembly to the tissue.

5. The electrosurgical device of claim 1, wherein the antenna assembly and the elongated body member are releasably coupled to each other.

6. The electrosurgical device of claim 1, further comprising a filling of electrically nonconductive material disposed within the opening.

7. The electrosurgical device of claim 1, wherein the elongated body member includes a tapered distal tip configured to penetrate tissue.

8. The electrosurgical device of claim 1, wherein the outer sleeve includes a plurality of apertures defined through a surface of the outer sleeve.

9. An electrosurgical device for treating tissue, the electrosurgical device comprising:
   an elongated body member including an electrically conductive outer jacket;
   an antenna assembly disposed within the elongated body member and configured to deliver electrosurgical energy to tissue; and
   an outer sleeve disposed about the elongated body member, at least one of the elongated body member or the outer sleeve movable relative to the other to control exposure of an opening in the elongated body member.

10. The electrosurgical device according to claim 9, wherein the elongated body member defines a chamber extending along a longitudinal axis defined by the elongated body member, at least a portion of the antenna assembly disposed within the chamber.

* * * * *